United States Patent
Prinz et al.

(10) Patent No.: US 6,541,652 B2
(45) Date of Patent: Apr. 1, 2003

(54) PROCESS AND APPARATUS FOR ISOLATING ORGANIC SUBSTANCES FROM A GAS MIXTURE IN WHICH THESE SUBSTANCES ARE PRESENT

(75) Inventors: Peter Prinz, Dormagen (DE); Josef Schmitz, Bedburg (DE); Gunter Schummer, Pulheim (DE); Rainer Strobel, Dormagen (DE); Arnd Stuwe, Leverkusen (DE)

(73) Assignee: BP Koln GmbH, Cologne (DE)

( * ) Notice: Subject to any disclaimer, the term of this patent is extended or adjusted under 35 U.S.C. 154(b) by 0 days.

(21) Appl. No.: 09/916,336

(22) Filed: Jul. 30, 2001

(65) Prior Publication Data

US 2002/0087023 A1 Jul. 4, 2002

(30) Foreign Application Priority Data

Aug. 3, 2000 (DE) .......................................... 100 37 774

(51) Int. Cl.$^7$ .............................................. C07C 255/08
(52) U.S. Cl. ...................................... 558/466; 558/463
(58) Field of Search ................................. 558/466, 463

(56) References Cited

U.S. PATENT DOCUMENTS 5,703,268 A * 12/1997 Wachtendorf et al. ...... 558/466
6,054,603 A * 4/2000 Godbole et al. ............ 558/466

* cited by examiner

*Primary Examiner*—Joseph K. McKane
*Assistant Examiner*—Golam M M Shameem
(74) *Attorney, Agent, or Firm*—Finnegan, Henderson, Farabow, Garrett and Dunner, L.L.P.

(57) ABSTRACT

Process for isolating one or more organic substances from a gas mixture in which these organic substances are present, in which the gas mixture is subjected to a quenching in a column, characterized in that quenching is carried out in the upper part of the column and the quenching liquid is subjected to stripping in the lower part of the column.

7 Claims, 1 Drawing Sheet

PROCESS AND APPARATUS FOR ISOLATING ORGANIC SUBSTANCES FROM A GAS MIXTURE IN WHICH THESE SUBSTANCES ARE PRESENT

BACKGROUND OF THE INVENTION

The invention relates to a process for isolating one or more organic substances from a gas mixture in which these organic substances are present, in which the gas mixture is subjected to quenching, and also to an apparatus for carrying out the process.

Many chemical production processes result in a reaction gas which comprises the desired reaction product and also further substances such as unreacted starting materials and undesired by-products. Since a considerable quantity of heat of reaction may be liberated in production processes from which the reaction gases are obtained, such reaction gases frequently have a high temperature. In industry, the reaction gases are usually cooled by use of heat exchangers. A fundamental distinction is made between "direct" and "indirect" heat exchange. In direct heat exchange, the stream is brought into direct contact with the heating or cooling medium.

An important example of such a direct cooling process is the quenching of pyrolysis gases by spraying oil directly into them. However, quenching is also employed for cooling hot reaction gases from the industrial production of acrylonitrile or methacrylonitrile by the Sohio process. The Sohio process involves the reaction of propylene or isobutene, oxygen and ammonia in one step over bismuth/molybdenum catalysts in a fluidized bed. The synthesis itself proceeds with liberation of a considerable quantity of heat of reaction, so that the reaction gases leaving the acrylonitrile or methacrylonitrile reactors have a very high temperature. In the quenching procedure, the hot reaction gas is then brought into direct contact with the liquid cooling medium, usually water. In this procedure, small amounts of organic gases are washed from the reaction gas in the quenching column.

Quenching apparatuses are known in a wide variety of designs. Thus, the reaction gas to be cooled and the cooling liquid can be conveyed either in cocurrent or in countercurrent.

The isolation of acrylonitrile or methacrylonitrile from the reaction gases and, in particular, achievement of an increase in the product yield is of high importance in industry.

U.S. Pat. No. 4,720,566 discloses, for example, the addition of a hydroxylamine and a phenylenediamine to the reaction gases of an acrylonitrile synthesis before they enter the quenching column so as to avoid undesirable polymerization of acrylonitrile in the quenching column and thus to increase the acrylonitrile yield.

U.S. Pat. No. 5,703,268 describes firstly quenching the reaction gases of an acrylonitrile or methacrylonitrile synthesis with water and subsequently passing the resulting cooled gas stream containing acrylonitrile or methacrylonitrile to an absorber column where the acrylonitrile or methacrylonitrile is brought into contact with water in countercurrent and absorbed by the water. To separate off the acrylonitrile or methacrylonitrile, the aqueous solution of acrylonitrile or methacrylonitrile is then passed through a first distillation column (recovery column) and the bottom product is subsequently passed through a second distillation column (stripper column). The process improvement of U.S. Pat. No. 5,703,268 comprises increasing the hydraulic capacity of the apparatuses by means of specific pressure increases in the two distillation columns.

U.S. Pat. No. 4,234,510 describes feeding the reaction gas which has been cooled in the quenching column firstly into a column provided with cooling elements in which a certain amount of acrylonitrile or methacrylonitrile is then condensed before the gas is introduced into the absorber column.

Furthermore, U.S. Pat. No. 3,936,360 discloses recirculating the bottom product obtained in the final distillation columns to the quenching column and utilizing it there as at least part of the quenching liquid.

The quenching apparatuses described in the abovementioned processes for cooling hot reaction gases have a disadvantage common to all of them. The quenching apparatuses are customarily constructed so that the quenching liquid is circulated and a bottom volume is present below the mixing zone of reaction gas and quenching liquid. An amount of quenching liquid which is sufficiently large for operation of the quenching liquid circulation pump is held in this bottom volume. This frequently results in long residence times of the quenching liquid in the bottom volume and in the pump circuit. However, such long residence times constitute a considerable disadvantage since undesirable reactions then occur between the components dissolved in the quenching liquid.

In the case of the acrylonitrile synthesis, a certain proportion of the acrylonitrile produced and of the ammonia is dissolved in the quenching liquid from the hot reaction gases during quenching. The acrylonitrile and ammonia present in the liquid then react with one another to form undesirable by-products, for example hydrolysis products of acrylonitrile and oligomers of acrylonitrile, sometimes also with ammonia which can be described by the following simplified structural formula: $[-NH_2-CH_2CH_2(CN)-]_x$. In this way, an amount of up to 3% of the acrylonitrile previously produced is lost again.

U.S. Pat. No. 3,876,508 discloses passing the reaction gases of an acrylonitrile synthesis into a quenching apparatus in which an aqueous solution of a mineral acid is used as quenching liquid. This leads to the ammonia dissolved in the quenching liquid being immediately neutralized to form corresponding ammonium salts and therefore not being able to react with likewise dissolved acrylonitrile to form undesirable by-products. However, the quenching liquid still has to be worked up, firstly to separate off the ammonium salts present therein and, secondly, to recover the approximately 3% of dissolved acrylonitrile. For this purpose, the quenching liquid is fed into a subsequent distillation or stripping column where, for successful distillation or stripping, it is absolutely necessary for the pH of the quenching liquid to be held at a value of not more than 5, preferably not more than 3, by addition of an acid. Only by means of this measure is it possible to suppress undesirable subsequent or polymerization reactions of the still dissolved acrylonitrile. Overall, this variant is complicated in terms of apparatus.

It is therefore an object of the present invention to provide a process by means of which organic substances, in particular acrylonitrile or methacrylonitrile, can be recovered and isolated without use of complicated apparatus and at the same time in high yield from reaction gases in which these substances, in particular acrylonitrile or methacrylonitrile, are present.

SUMMARY OF THE INVENTION

The invention accordingly provides a process for isolating one or more organic substances from a gas mixture in which these organic substances are present, in which the gas mixture is subjected to a quenching in a column, characterized in that quenching is carried out in the upper part of the column and the quenching liquid is subjected to stripping in the lower part of the column.

In the process of the present invention, the gas mixture introduced is quenched in the upper part of the column by bringing it into intimate contact with a stream of quenching liquid. This results in rapid cooling of the gas mixture fed in. The stream of quenching liquid is subsequently subjected to stripping in the lower part of the column by bringing the quenching liquid into contact with an inert gas. As a result, the organic substances dissolved in the quenching liquid are carried from the column with the inert gas.

In the process of the invention, preference is given to using a gas mixture from an acrylonitrile or methacrylonitrile synthesis.

The invention further provides a column for carrying out the process of the invention, in which both quenching and stripping can be carried out and which is characterized in that a) it has an upper quenching section and a lower stripping section, b) it has a lateral feed facility for a reaction gas stream below the quenching section and, above the quenching section, a further lateral feed line for the quenching liquid, c) it has, above the quenching section, a liquid distributor through which the quenching liquid is introduced into the column, d) a feed line for the stripping gas is located below the stripping section and is arranged either above the bottom volume of the column or else at the height of the bottom volume, e) the bottom volume of the column is connected to the liquid distributor of the quenching section via a pump-driven feed line and f) optionally, part of the bottom volume can be discharged from the column via a lateral discharge line, g) a feed line for fresh quenching liquid is present at the height of the bottom volume and h) a discharge line for discharge of the product gas stream is located at the top of the column.

DETAILED DESCRIPTION OF THE INVENTION

Figure 1:
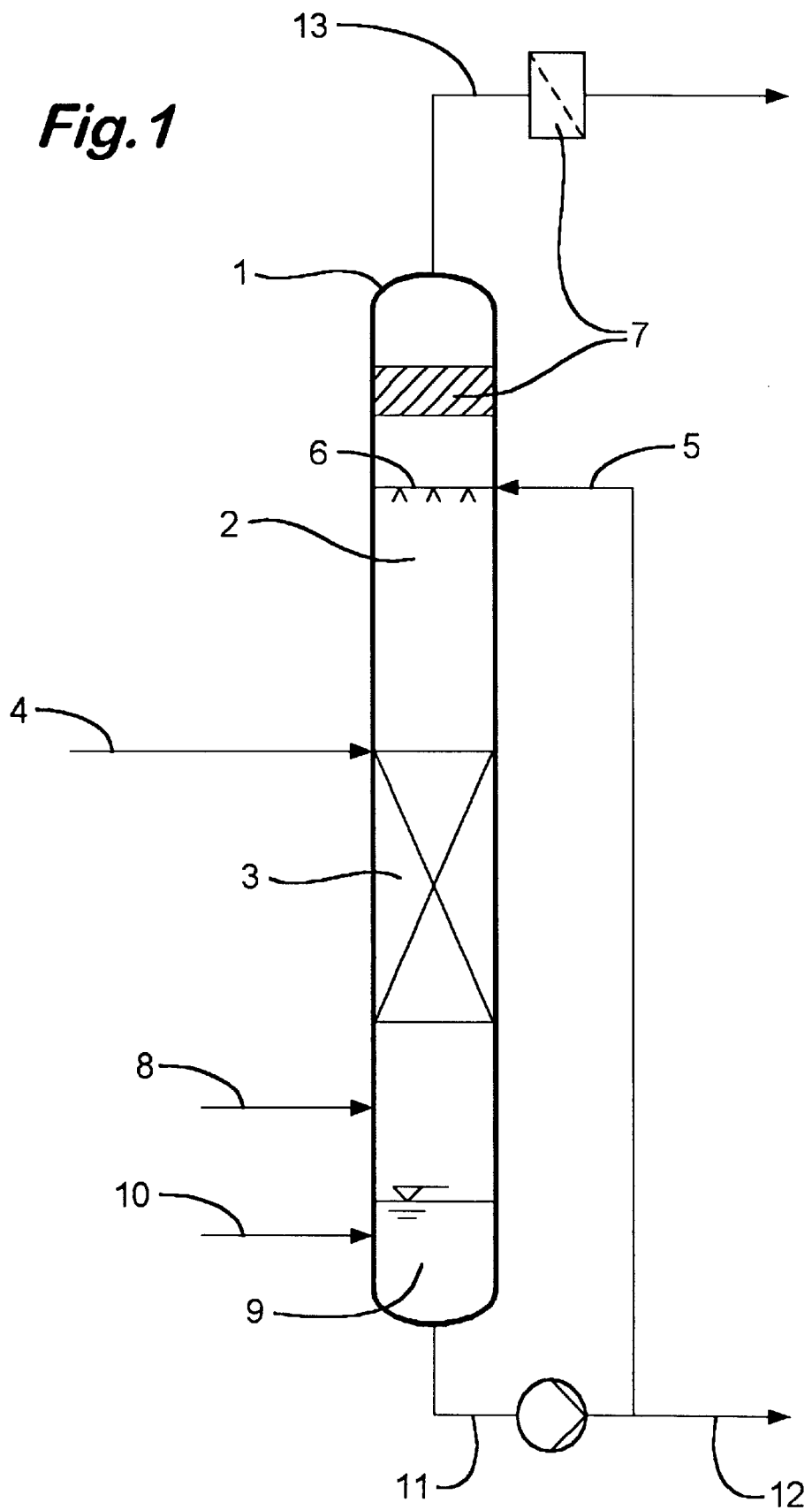
FIG. 1 shows, by way of example, an embodiment of the apparatus of the invention by means of which the process of the invention can be carried out.

The apparatus of the invention consists essentially of a column body (1).

a) This column body comprises an upper quenching section (2) and a lower stripping section (3).

b) The gas stream to be cooled is fed in laterally via the feed line (4) below the quenching section (2). Above this lateral feed line (4) for the gas stream, there is located a further lateral feed line (5) for the quenching liquid. The quenching section is thus the part of the column of the invention between the feed line (4) for the reaction gas stream and the feed line (5) for the quenching liquid located above it.

c) The quenching liquid is introduced into the gas stream to be cooled in countercurrent via a liquid distributor (6). A droplet precipitator (7) is advantageously located in the quenching section of the column above the liquid distributor (6). This serves to precipitate liquid droplets entrained in the gas stream. Depending on the product properties of gas and quenching liquid, the droplet precipitator used can be an impingement precipitator, a separation collar or a lamella or wire mesh construction of any type (e.g. steel wool). In addition, a further droplet precipitator can also be located outside the column in the gas offtake line, but it can also be entirely omitted or located exclusively outside the column in the gas offtake line. In the column, the quenching liquid is uniformly distributed across the column cross section by means of the liquid distributor (6), preferably by means of one or more spray nozzles. The liquid then descends as droplets in countercurrent to the gas stream, is heated to the boiling point during the contact time with the gas and partly vaporises. This results in the corresponding quantity of heat being withdrawn from the gas, thereby cooling the gas. At the same time, the quenching liquid is enriched to a certain extent with components from the gas stream. The enriched liquid descends to the stripping section (3) of the column. The quenching section can be operated without or with commercial internals such as sieve trays or packing.

d) Below this stripping section there is located a feed line (8) for the stripping gas. This stripping gas can be fed in either above the bottom volume (9), as shown in FIG. 1, or else into the liquid phase at the bottom. The stripping gas is conveyed upwards through the stripping section in countercurrent to the quenching liquid. In the process, the stream of stripping gas takes up the components dissolved in the quenching liquid and is taken from the column together with the cooled gas. Depending on the product properties of the liquid, the stripping section of the column can be equipped with random packing, ordered packing or separation trays of any type. The quenching liquid is collected in the bottom (9) of the column which serves as pump reservoir.

e) The bottom volume of the column is connected via a pump-operated line (11) to the liquid distributor (6) of the quenching section. The major part of the quenching liquid from the bottom volume is thus fed back to the liquid distributor.

f) A smaller part of the quenching liquid is optionally discharged from the circuit via the line (12) in order to prevent accumulation of polymeric constituents and impurities.

g) The liquid taken from the quench circuit via line (12) and the liquid vaporised in the quenching section is fed back into the bottom of the column in the form of fresh quenching liquid via the feed line (10).

h) The top of the column is provided with a discharge line (13) for the discharge of the product gas stream.

The process of the invention and the apparatus of the invention are preferably used for the work-up of reaction gases from an acrylonitrile or methacrylonitrile synthesis.

The process of the invention and the corresponding column are particularly suitable for the work-up and cooling of reaction gases from an acrylonitrile synthesis.

The reaction gases formed in the synthesis of acrylonitrile comprise, firstly, the desired acrylonitrile and, secondly, unreacted starting materials, i.e. propylene, ammonia, oxygen and nitrogen, and also certain amounts of HCN, $CO_2$, CO, acetonitrile, acrolein, acrylic acid, acetone and possibly fumaronitrile, nicotinonitrile, oxazole, acetic acid, water, further higher nitriles, aldehydes and ketones. In addition, small amounts of other unknown organic substances can also be present in the reaction gas. A typical composition of a reaction gas from the synthesis of acrylonitrile is shown in the following table:

| % by volume | Component |
|---|---|
| greater than 50 | nitrogen |
| from 1 to 50 | acrylonitrile, oxygen, HCN, $CO_2$, CO |
| less than 1 | ammonia, propylene, acetonitrile, acrolein, acetic acid |
| traces | acetaldehyde, propionitrile, acetone, acrylic acid |

The reaction gases formed in the synthesis of methacrylonitrile analogously comprise, firstly, the desired methacrylonitrile and, secondly, unreacted starting materials, i.e. isobutene, ammonium, oxygen and nitrogen and also certain amounts of HCN, $CO_2$, CO, propionitrile, methacrolein, methacrylic acid, water, further higher nitriles, aldehydes and ketones and, depending on the feedstock stream, also isobutane and other $C_4$-hydrocarbons.

Polymerization inhibitors such as hydroxylamines or phenylenediamine can also be added to these reaction gases from the synthesis of acrylonitrile or methacrylonitrile, as described in U.S. Pat. No. 4,720,566.

The synthesis of acrylonitrile/methacrylonitrile is carried out in a manner known to those skilled in the art. Comprehensive details of the procedure for the synthesis of acrylonitrile may be found, for example in Ullmann's Encyclopedia of Industrial Chemistry, Vol. A1, 5th edition, pp. 177–184, VCH-Verlagsgesellschaft, FRG-Weinheim, 1985, or in K. Weissermel, H. J. Arpe, "Industrielle organische Chemie", 5th edition, pp 332–341, Wiley-VCH, FRG-Weinheim, 1998. The synthesis of methacrylonitrile is likewise described in K. Weissermel, H. J. Arpe, "Industrielle organische Chemie", 5th edition, p. 312, Wiley-VCH, FRG-Weinheim, 1998, and, for example, in GB-A-1 238 347.

The quenching liquid used is usually water. Here, about 0.5–8 kg, preferably 0.7–5 kg, particularly preferably 0.8–2 kg and in particular 1–2 kg, of quenching liquid are used per $m^3$ of reaction gas, with about 10–15% of the quenching liquid vaporising during quenching. The lower limit is determined by the energy balance, i.e. at least the amount which vaporises plus a certain amount which collects at the bottom have to be circulated by pumping and also the amount which vaporises has to be fed back into the system as fresh quenching liquid. The upper limit is determined by the liquid throughput limit of the column or the hydraulics.

The temperatures at the top of the quench stripper are established in accordance with the thermodynamics of the system, i.e. they are determined by the boiling point of the quenching liquid at the operating pressure. The temperature of the stripping gas or the quenching liquid in the stripping section influences the separation performance and therefore has to be taken into account in the design of the quench stripper.

The quenching liquid fed in above the quenching section via line (5) usually has a temperature of 70–100° C. This temperature is established as a function of the temperature of the reaction gas, the pressure, the mass flows and the heat losses in the quenching water circuit. The reaction gas introduced via line (4) has a temperature of 200–300° C., preferably 210–280° C. and particularly preferably 225–250° C.

The stripping gas used is usually an inert gas, preferably nitrogen. The use of the absorber waste gas from the absorption in the acrylonitrile synthesis as inert gas has also been found to be useful.

The amount of inert gas used as a function of the amount of propylene or isobutylene used in the synthesis of acrylonitrile or methacrylonitrile. It is usual to use 0.1–5 mol, preferably 0.5–3 mol and in particular 0.75–1.5 mol of inert gas per mole of propylene or isobutene. Based on the sum of the reaction gases (i.e. the gases ammonia, propylene and air used in the synthesis of acrylonitrile), this corresponds to a proportion of 1–60% by volume, preferably 6–36% by volume and in particular 12–18% by volume, of inert gas.

The stripping gas is fed into the column of the invention below the stripping section via a lateral feed line. It can be fed in above the bottom volume, but it is in principle also possible to feed it directly into the liquid phase at the bottom. However, the stripping gas is preferably fed in at a distance of about 1–2 times the column diameter above the liquid phase and at the same time 1–2 times the column diameter below the first internals of the stripping section. The temperature of the stripping gas is usually in the range 0–100° C.

The dimensions of the stripping section are designed so that virtually quantitative separation of the product from the quenching liquid is achieved.

The size, i.e. the height of the column of the invention and the length ratio of the stripping section to the quenching section, is designed so that the required number of theoretical plates is obtained. The column diameter is determined by the hydraulic throughput data of the liquid stream and the stripping gas stream.

The bottom discharge, i.e. the part of the bottom volume discharged via the line (12), is usually selected so that the evaporation residue of this bottom discharge, which comprises primarily polymeric constituents, by-products and salts, is 5–50% by weight, preferably 10–35% by weight and particularly preferably 20–25% by weight, based on the bottom discharge.

The column of the invention represents a synergistic combination of the two process engineering measures of quenching (cooling a hot gas stream by mixing with a liquid) and stripping (driving dissolved components out of a liquid by mixing with a gas stream). The column is therefore also referred to as a quench stripper. The downstream stripping process essentially frees the quenching liquid of the dissolved, volatile components, in particular acrylonitrile, before it reaches the bottom volume. As a result, the residence times of the dissolved components in the quenching liquid are significantly reduced compared with conventional quenching apparatuses. In this way, it is possible, in particular, to suppress the undesirable secondary reaction between acrylonitrile and ammonia and reduce the acrylonitrile losses to 1% or less of the achieved yield, so that the composition of the product gas stream is essentially identical to the composition of the reaction gas fed in.

EXAMPLE

I Synthesis of Acrylonitrile

An experimental reactor having a diameter of 3.4 cm and a length of 100 cm (reaction volume: 1.4 liters) is charged with 550 g of a Bi/Mo mixed oxide catalyst customarily used for ACN production and heated to a temperature of 400–450° C. About 150 standard l/h of air together with about 16 standard l/h of propylene and about 20 standard l/h of ammonia are subsequently fed in from below.

II Quench Stripping

The quench stripper according to the invention located downstream of the experimental acrylonitrile reactor has a diameter of 3.2 cm and a length of 72 cm. The volume of packing in the quenching section is 0.2 liters and the volume of packing in the stripping section is 0.185 liters.

The temperature of the reaction gases leaving the top of the acrylonitrile reactor is 250° C.; at this temperature, the gas stream is introduced laterally into the quench stripper. A temperature of about 73° C. is set in the quenching section of the column and a temperature of 75–76° C. is set in the stripping section of the column. The temperature at the bottom of the quench stripper is about 76° C. The amount of inert gas fed in laterally below the stripping section can be varied and is 0.1–5.0 mol of nitrogen per mol of propylene.

We claim:

1. A process for isolating one or more organic substances from a gas mixture in which these one or more organic substances are present, comprising quenching a gas mixture containing one or more organic substances by bringing it into intimate contact with a stream of quenching liquid in an upper part of a column and subsequently stripping the quenching liquid of one or more of said organic substances by bringing the quenching liquid into contact with an inert gas in a lower part of the column.

2. The process according to claim 1 wherein the gas mixture originates from an acrylonitrile or a methacrylonitrile synthesis.

3. The process according to claim 2, wherein the gas mixture formed in the acrylonitrile synthesis comprises acrylonitrile, propylene, ammonium, oxygen, nitrogen, HCN, $CO_2$, CO, acetonitrile, acrolein, or acrylic acid.

4. The process according to claim 1, wherein 0.5–8 kg, 0.7–5 kg, 0.8–2 kg or 1–2 kg of quenching liquid are used per m3 of gas mixture.

5. The process according to claim 2, wherein 0.1–5 mol, 0.5–3 mol or 0.75–1.5 mol of inert gas are used per mol of propylene/isobutene employed in the synthesis of acrylonitrile or methacrylonitrile.

6. The process according to claim 1, wherein the inert gas used is absorber waste gas from the absorption in the synthesis of acrylonitrile.

7. The process according to claim 4, wherein the quenching liquid is water.

* * * * *

UNITED STATES PATENT AND TRADEMARK OFFICE
CERTIFICATE OF CORRECTION

PATENT NO. : 6,541,652 B2
APPLICATION NO. : 09/916336
DATED : April 1, 2003
INVENTOR(S) : Peter Prinz et al.

It is certified that error appears in the above-identified patent and that said Letters Patent is hereby corrected as shown below:

Title page, item [73], "Assignee: BP Koln GmbH, Cologne (DE)" should read --Assignee: BP Koln GmbH, Cologne (DE) and Bayer AG, Leverkusen (DE)--.

Signed and Sealed this

Eighth Day of May, 2007

JON W. DUDAS
*Director of the United States Patent and Trademark Office*